(12) United States Patent
Sullivan

(10) Patent No.: US 6,241,518 B1
(45) Date of Patent: Jun. 5, 2001

(54) APPARATUS AND METHOD FOR PREVENTING TOOTH GRINDING IN PATIENTS WEARING BRACES

(76) Inventor: Terrence C. Sullivan, 805 164th St. SE., Mill Creek, WA (US) 98012-6316

( * ) Notice: Subject to any disclaimer, the term of this patent is extended or adjusted under 35 U.S.C. 154(b) by 0 days.

(21) Appl. No.: 09/444,544

(22) Filed: Nov. 22, 1999

(51) Int. Cl.[7] ................................................ A61C 5/14
(52) U.S. Cl. ........................ 433/22; 433/140; 128/861
(58) Field of Search ........................ 433/6, 140, 22; 128/848, 859, 860, 861, 862

(56) References Cited

U.S. PATENT DOCUMENTS

| | | | |
|---|---|---|---|
| 3,457,916 | * | 7/1969 | Wolicki .................. 128/662 |
| 3,837,081 | * | 9/1974 | Kesling ...................... 433/6 |
| 4,512,740 | * | 4/1985 | Kurz ............................ 433/6 |
| 4,976,618 | * | 12/1990 | Anderson ................... 433/6 |
| 5,037,296 | * | 8/1991 | Karwoski .................. 433/6 |
| 5,173,048 | * | 12/1992 | Summer ..................... 433/6 |
| 5,386,821 | * | 2/1995 | Poterack .................. 128/661 |
| 5,490,520 | * | 2/1996 | Schaefer .................. 128/848 |
| 5,954,500 | * | 9/1999 | Spriggs ....................... 433/6 |

* cited by examiner

*Primary Examiner*—Todd E. Manahan
(74) *Attorney, Agent, or Firm*—Davis Wright Tremaine LLP

(57) ABSTRACT

The present invention provides an apparatus and method for preventing grinding of the upper and lower teeth of a person wearing braces. The apparatus provides a bite guard adapted to prevent grinding of the teeth of a person wearing braces, the bite guard comprising a U-shaped base having a first surface, a second surface, a U-shaped inner side, and a U-shaped outer side, and a width at least as wide as the person's teeth, and a plurality of flexible hooks attached to the outer side and projecting at a first selected angle relative to a direction normal to the first surface. The method provides a way for preventing dental grinding of occlusal surfaces of a patient wearing braces, the method comprising positioning a bite guard between the occlusal surfaces of the patient's upper and lower teeth, and attaching the insert to the patient's braces on the upper or lower teeth.

13 Claims, 2 Drawing Sheets

APPARATUS AND METHOD FOR PREVENTING TOOTH GRINDING IN PATIENTS WEARING BRACES

FIELD OF THE INVENTION

This invention relates to an apparatus and method for preventing teeth from grinding together, and in particular to an apparatus and method for preventing teeth from grinding together in patients wearing braces.

BACKGROUND

Grinding between a patient's upper and lower teeth can present a serious dental health problem. Often caused by stress, and usually occurring at night, grinding teeth result from tightly clenched jaw muscles, which force together the occlusal surfaces of the upper and lower teeth. In addition to the clenching action, the jaw muscles cause the upper and lower teeth to move relative to each other while they are being forced into contact, thus causing grinding. This grinding can cause serious damage to a person's teeth. In the short term, the constant grinding can wear enamel off tooth surfaces. Over a long period of time, the grinding can wear through the enamel and into the tooth pulp, causing more serious damage. Moreover, the clenched muscles that cause the grinding can, when chronic, lead to more serious conditions such as temporal mandibular joint (TMJ) disorder.

Presently, the only method for preventing teeth from grinding together is to prevent the occlusal surfaces of the teeth from contacting one another. This is usually accomplished by inserting a "bite guard" between the occlusal surfaces of the upper and lower teeth. Bite guards are also known as night guards, occlusal splints, bruxism splints, TMJ/TMD splints, and gnathological splints. Bite guards are usually custom-fitted devices made by taking a mold of the person's upper or lower teeth and manufacturing a device which closely conforms to, and fits over, the teeth. Since they are tight-fitting, bite guards stay in place by snapping onto the contours of the teeth.

Although they do a good job of addressing the problem of tooth grinding, presently available bite guards have an important limitation: they cannot be worn by persons who are wearing braces. Mostly, this is because the hardware associated with braces (brackets, bands and archwires) are cemented to the teeth, thus preventing the bite guard from conforming to, or attaching to, the contours of the teeth. Even if they could be used with braces, present bite guards are undesirable for use with braces because of their close fit, which would prevent the tooth movement the braces are designed to cause. Thus, persons wearing braces who are having problems with tooth grinding are left without recourse. For these reasons, there is a need in the art for a bite guard that is compatible with braces.

SUMMARY OF THE INVENTION

The present invention provides an apparatus and method for preventing grinding of the upper and lower teeth of a person wearing braces. The apparatus provides a bite guard adapted to prevent grinding of the teeth of a person wearing braces, the bite guard comprising a U-shaped base having a first surface, a second surface, a U-shaped inner side, and a U-shaped outer side, and a width at least as wide as the person's teeth, and a plurality of flexible hooks attached to the outer side and projecting at a first selected angle relative to a direction normal to the first surface. The method provides a way for preventing dental grinding of occlusal surfaces of a patient wearing braces, the method comprising positioning a bite guard between the occlusal surfaces of the patient's upper and lower teeth, and attaching the insert to the patient's braces on the upper or lower teeth.

DETAILED DESCRIPTION OF THE INVENTION

Described below is an embodiment of the present invention. The embodiment illustrates ways in which the present invention can be implemented. In the description that follows, like numerals represent like elements in all figures. For example, where the numeral 10 is used to refer to a particular element in one figure, the numeral 10 appearing in any other figure refers to the same element.

Figure 1:
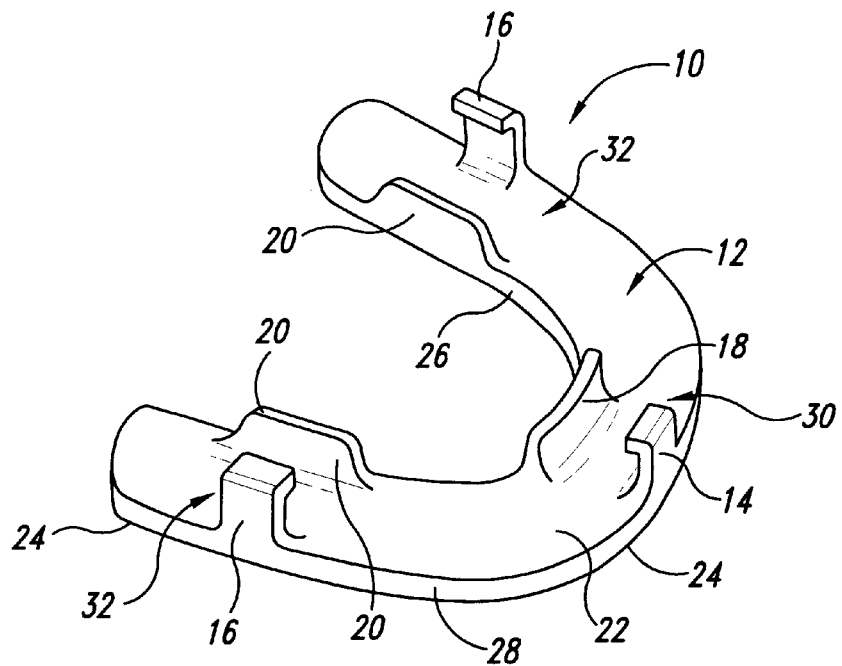
FIG. 1 is a perspective view of an embodiment of the present inventive bite guard.

FIG. 1 illustrates an embodiment of the inventive bite guard. The bite guard 10 comprises a generally U-shaped base 12 and a plurality of hooks 14 and 16 which are adapted to attach the bite guard 10 to the arch wires of the braces, thus securing the bite guard along the occlusal plane between the patient's upper and lower teeth. The bite guard 10 also includes a plurality of flanges 18 and 20 extending from the base 12; these flanges help prevent the bite guard 10 from becoming dislodged due to lateral or anterior-posterior grinding of the patient's teeth. The entire bite guard 10 may be made of any material softer than tooth enamel, but is preferably made of a soft rubber for flexibility and patient comfort. Both the hooks 14 and 16 and the flanges 18 and 20 are integrally molded into the base.

The base 12 is typically contained in a single plane (i.e., flat) and has a first surface 22, a second surface 24, an inner (lingual) side 26 and an outer (labial) side 28. When the bite guard is attached to braces on the patient's lower teeth, the first surface 22 wi0 ll be a lower surface in contact with the occlusal surfaces of the lower teeth, and the second surface 24 will be an upper surface in contact with the occlusal surfaces of the upper teeth. When the bite guard is attached to braces on the patient's upper teeth, the reverse is true: the first surface 22 is an upper surface and the second surface 24 is a lower surface. The base need not be flat, though; it may have some contouring to adapt to the shape of the patient's teeth.

Figure 2:
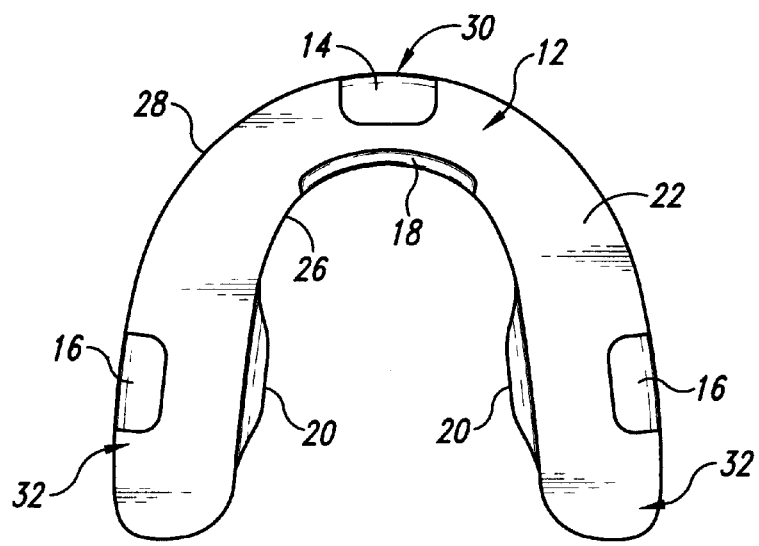
FIG. 2 is a top view of the bite guard shown in FIG. 1.

FIG. 2 illustrates the shape of the base and the arrangement on the base of the plurality of hooks 14 and 16 and the plurality of flanges 18 and 20. The shape of the base 12 is designed so that the base will fit along the occlusal locus of the person's teeth. The occlusal locus is a generally U-shaped curve resulting from connecting the occlusal surfaces of the person's teeth, i.e., all points at which the upper teeth contact the lower teeth. The width of the base, which is the distance between the inner (lingual) side 26 and the outer (labial) side 28, is at least as wide as the person's teeth.

The generally U-shaped base 12 comprises a vertex portion 30 and a couple of straight lateral portions 32. The hooks are attached to the base along the outer (labial) side 28. preferably, the hooks are arranged as shown, with a front hook 14 at the vertex of the base, and a pair of lateral hooks 16 located along the straight lateral portions of the base. The flanges comprise a front flange 18 and a pair of lateral flanges 20 attached to the base along the inner (lingual) side 26 of the base. Preferably, the flanges are positioned on the inner (lingual) side directly opposite where the hooks are attached to the outer (labial) side, with the front flange 18 at the vertex 30 of the base and the lateral flanges along the straight lateral portions 32 of the base.

Figure 3:
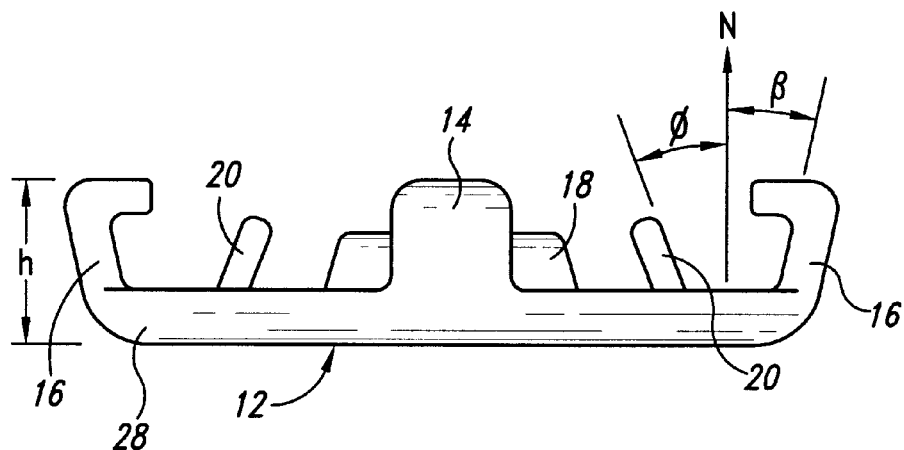
FIG. 3 is a front view of the bite guard shown in FIG. 1.

FIG. 3 illustrates the positions of the hooks 14 and 16 and the flanges 18 and 20. The hooks are attached to the base along the outer (labial) side 28 and project from the base at a selected angle β relative to a direction approximately normal to the base, i.e., relative to the normal vector N. The front hook 14 and lateral hooks 16 need not have the same angle β; the front hook 14 may have a different value of β than the lateral hooks 16, and each lateral hook 16 may have its own different value for β. The angle β is preferably about 27 degrees, but may range between about 0 degrees and about 45 degrees. It may be desirable to build the bite guard 10 such that the angle β has a small positive value. That way, when the hook is bent inwardly to attach to the arch wire of the braces, a small reactive moment will be induced in the hook, which will secure the hooks 14 and 16 to the arch wires. The hooks 14 and 16 have a height h measured from the first surface. The height h is slightly less than the distance between the occlusal surface of the tooth and the arch wire of the braces. Since the hooks 14 and 16 are made of a flexible material, they can be stretched until they attach to the braces. This stretching induces tensile loads in the hooks, which then help keep the bite guard firmly in place in the patient's mouth.

The front flange 18 and lateral flanges 20 are similarly attached to the base along the inner (lingual) side 26 and project from the base at a selected angle φ relative to the normal vector N. The flanges 18 and 20 need not have the same angle φ; the front flange 18 may have a different value of φ than the lateral flanges 20, and each lateral flange 20 may have its own different value for φ. The angle φ is preferably about 27 degrees but may vary between about 0 degrees and about 45 degrees.

Figure 4:
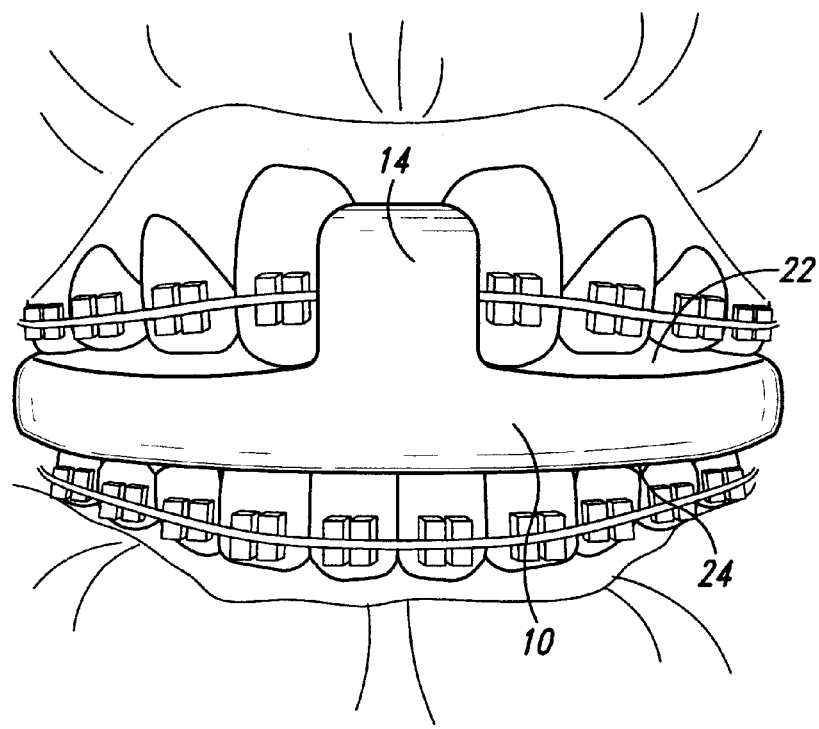
FIG. 4 is a front view of the bite guard of FIG. 1 in its operative position on the occlusal plane between the upper and lower teeth of a patient.

FIG. 4 illustrates the use of the bite guard 10. The bite guard 10 is simply inserted between the patient's upper and lower teeth such that the occlusal surfaces of the teeth are in contact with the base, i.e., such that the bite guard rests on the occlusal plane. The bite guard 10 must be inserted in the desired orientation, with the hooks 14 and 16 positioned upward or downward, depending on whether they will be attached to braces on the upper or lower teeth. Once correctly positioned, the hooks are attached to the arch wires of the braces and the installation is complete.

The bite guard 10 a single piece created by injection molding of the desired soft, rubber-like material. A mold is created having the desired shape and size, and the material is injected into the mold and allowed to set.

An embodiment of the present invention has been described above. A person skilled in the art, however, will recognize that many other embodiments are possible within the scope of the invention. For this reason, the scope of the invention is not to be determined from the description of the embodiment, but must instead be determined solely from the following claims.

What is claimed is:

1. A bite guard adapted to prevent grinding of the teeth of a person wearing braces, the bite guard comprising:

a U-shaped base contained in a single plane and having a first surface, a second surface, a U-shaped inner side, and a U-shaped outer side, and a width at least as wide as the person's teeth; and a plurality of flexible hooks attached to the outer side and projecting at a first selected angle relative to a direction normal to the first surface, wherein the hooks are attachable to the braces.

2. The bite guard of claim 1 wherein the plurality of flexible hooks comprises three hooks attached to the base at a vertex and along each of two legs of the U-shaped outer side.

3. The bite guard of claim 1 wherein the first selected angle is between about 0 degrees and about 45 degrees.

4. The bite guard of claim 1 further comprising a plurality of flanges attached to the inner side and projecting at a second selected angle relative to a direction normal to the first surface.

5. The bite guard of claim 4 wherein the second selected angle is between about 0 degrees and about 45 degrees.

6. A bite guard adapted to prevent grinding of the teeth of a person wearing braces, the bite guard comprising:

a base contained in a single plane and shaped like an occlusal locus of the person's teeth, the base having a first surface, a second surface, a lingual side and a labial side, and a width at least as wide as the person's teeth;

a plurality of hooks attached to the base along the labial side and projecting therefrom at a first selected angle relative to a direction normal to the first surface wherein the hooks are attachable to the braces; and a plurality of flanges attached to the base along the lingual side and projecting therefrom at a second selected angle relative to a direction normal to the first surface.

7. The bite guard of claim 6 wherein the plurality of flexible hooks comprises one hook attached to the labial side of the base at a vertex of the base, and a pair of hooks attached to the labial side of a straight part of the base.

8. The bite guard of claim 6 wherein the first selected angle is between about 0 degrees and about 45 degrees.

9. The bite guard of claim 6 wherein the second selected angle is between about 0 degrees and about 45 degrees.

10. A method for preventing dental grinding of occlusal surfaces of a patient wearing braces, the method comprising:

positioning a bite guard between the occlusal surfaces of the patient's upper and lower teeth; and attaching the insert to the patient's braces on the upper or lower teeth.

11. The method of claim 10 wherein the bite guard comprises:

a U-shaped base having a first surface, a second surface, a U-shaped inner side, and a U-shaped outer side, and a width at least as wide as the person's teeth; and a plurality of flexible hooks attached to the outer side and projecting at a first selected angle relative to a direction normal to the first surface.

12. The method of claim 10 wherein attaching the bite guard to the patient's braces comprises attaching a plurality of hooks on the bite guard to an arch wire of the braces.

13. The method of claim 10 further comprising limiting a motion of the bite guard in the patient's mouth.

* * * * *